US00PP18751P2

(12) United States Plant Patent
Bradford

(10) Patent No.: US PP18,751 P2
(45) Date of Patent: Apr. 22, 2008

(54) NECTARINE TREE NAMED 'AUTUMN BRIGHT'

(50) Latin Name: *Prunus persica*
Varietal Denomination: Autumn Bright

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,896

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP6,363 P * 11/1988 Bradford et al.
PP13,475 P2 * 1/2003 Bradford

* cited by examiner

*Primary Examiner*—Kent Bell

(57) ABSTRACT

The present invention relates to a new and distinct variety of nectarine tree, *Prunus persica,* broadly characterized by a medium size, moderately vigorous, hardy, self-fertile, productive and regular bearing tree. The fruit matures under the ecological conditions described in mid September, with first picking on Sep. 12, 2006. The fruit is uniformly large in size, acidic and sweet in flavor, globose to slightly oblong in shape, clingstone in type, firm in texture, yellow in flesh color, and mostly red in skin color.

1 Drawing Sheet

Botanical classification: *Prunus persica.*
Variety denomination: 'AUTUMN BRIGHT'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'AUTUMN BRIGHT'.

During the spring of 1999 I gathered fruit from a 'September Bright' (U.S. Plant Pat. No. 13,475) nectarine tree in may experimental orchard located near Le Grand, Calif., in Merced County (San Joaquin Valley). I removed the seeds from the fruit, stratified, germinated, and grew them as seedlings on their own root in my greenhouse, and upon reaching dormancy that fall transplanted them to a cultivated area in the experimental orchard described above. During the fruit evaluation season of 2003 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to its parent, 'September Bright' (U.S. Plant Pat. No. 13,475) nectarine, by producing nectarines that are firm in texture, clingstone in type, yellow in flesh color, and mostly red in skin color, but is distinguished therefrom by producing fruit that matures about seven days later.

SUMMARY OF VARIETY

In summary, the present variety is characterized by a medium size, moderately vigorous, hardy, self-fertile, productive and regular bearing tree. The fruit matures under the ecological conditions described in mid September, with first picking on Sep. 12, 2006. The fruit is uniformly large in size, acidic and sweet in flavor, globose to slightly oblong in shape, clingstone in type, firm in texture, yellow in flesh color, and mostly red in skin color.

DRAWING

The accompanying photograph consists of four whole fruits positioned to display the characteristics of the skin color and form, one fruit divided transversely to the suture plane to reveal the flesh and stone, various leaves, and two insets showing buds and blossoms in various stages.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif. and was developed at the state of shipping ripe on Sep. 16, 2006, on the original tree during its seventh growing season. All major color code designations are by reference to the Inter-Society Color Council, National Bureau of Standards. Common color names are also used occasionally.

Tree

Size: Medium, reaching and maintaining a height of 8' [2.44 m.] and a spread of 9' [2.74 m.] after seven growing seasons utilizing typical dormant pruning.

Vigor: Medium, responding typically to irrigation and fertilization. The variety grows about 2' [0.61 m.] of surplus top-growth during the spring and summer. The plant should be grown on a standard commercial rootstock for production purposes.
Growth: Spreading and dense.
Form: Vase formed.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 650 hours.
Trunk:
*Size.*—Medium, reaching a maximum diameter of 3½" [89 m.] after the seventh growing season.
*Texture.*—Shaggy.
*Bark color.*—A Dark grayish yellowish brown [81. d.gy.yBr] and Moderate brown [58. m.Br] variegation.
*Lenticels.*—Approximate Number Per Square Inch: 10. Color: Dark orange yellow [72. d.OY]. Typical Size: ⅛" [3.2 mm.] to 7/16" [11.1 mm.]. Shape: Eye-shaped to elongated.
Branches:
*Size.*—Diameter of limb is 2¼" [57 mm.] measured 12" above the crotch, 1¼" [32 mm.] measured 12" above the first fork.
*Texture.*—Smooth on first and second year wood, increasing roughness with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Number Per Square Inch: More than 60 on second year wood. Color: Moderate orange yellow [71. m.OY]. Typical size: 1/32" [0.8 mm.] to 3/32" [2.4 mm.] on second year wood. Shape: Elongated.
Leaves:
*Size.*—Medium. Average length: 5¾" [146 mm.]. Average Width: 1⅝" [41 mm.].
*Arrangement.*—Alternate.
*Thickness.*—Medium.
*Form.*—Elliptical.
*Apex.*—Acuminate.
*Base.*—Acute, with a base angle of 70 to 80 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Vein color.*—Pale yellow green [121. p.YG].
*Petiole.*—Average Length: ½" [12.7 mm.]. Average Thickness: 1/16" [1.6 mm.]. Color: Light yellow green [119. l.YG].
*Stipules.*—Number: 2 per leaf, up to 6 per growing tip. Average Length: ⅜" [9.5 mm.]. Color: Brilliant yellow green [116. brill.YG] becoming Dark grayish reddish brown [47. d.gy.rBr] with maturity.
*Glands.*—Number: 2 to 6 per leaf. Position: Both alternate and opposite with the first two positioned on petiole and the rest on the base of blade. Size and Form: Very small on young leaves and actually appear to be globose, but mature into large reniform with age. Color: Brilliant yellow green [116. brill.YG] becoming Dark yellowish brown [78. d.yBr] with age.
*Leaf buds.*—Pointed, medium in size.
Flower buds:
*Hardiness.*—Hardy, with respect to central California winters.
*Diameter.*—Typically ¼" [6.4 mm.] 1 week before bloom.
*Length.*—Typically ⅜" [9.5 mm.] 1 week before bloom.
*Form.*—Not appressed.
*Surface.*—Pubescent.
*Color.*—Deep pink [3. deep Pk].
Flowers: Perfect, complete, perigynous, usually a single pistil, typically 24 or more stamens, five sepal and petal locations alternately positioned.
*Type.*—Small.
*Average flower diameter.*—⅞" [22.2 mm.].
*Number of petals.*—Five, a few with extra petal fragments, double blossoms rarely observed.
*Petal shape.*—Oval.
*Petal margin.*—Wavy.
*Average petal diameter.*—7/16" [11.1 mm.].
*Average petal length.*—9/16" [14.3 mm.].
*Petal apex.*—Rounded.
*Petal base.*—Acute.
*Petal color.*—Light purplish pink [249. l.pPk] toward the apex with Strong purplish red [255. s.pR] toward the margin.
*Anther color.*—Dark yellowish pink [30. d.yPk] over a Light yellow [86. l.Y] center.
*Stigma color.*—Light greenish yellow [101. l.gY].
*Sepal color.*—Dark purplish red [259. d.pR].
*Sepal length.*—¼" [6 mm.].
*Sepal width.*—3/16" [5 mm.].
*Average pistil length.*—11/16" [17.5 mm.], often protruding out of the bud before onset of bloom.
*Average Stamen length.*—7/16" [11.1 mm.].
*Fragrance.*—Moderate.
*Blooming period.*—Medium, with 'August Red' (U.S. Plant Pat. No. 6,363) nectarine.
*Onset of bloom.*—One person on Feb. 28, 2006.
*Date of full bloom.*—Mar. 10, 2006.
*Duration of bloom.*—One to two weeks, dependent on ambient temperature.
*Number per cluster.*—1 to 3 with single flowers most common.

FRUIT

Maturity When Described: Shipping ripe, Sep. 16, 2006.
Date of First Picking: Sep. 12, 2006.
*Date of Last Picking: Sep.* 20, 2006.
Size: Uniform, large.
*Average diameter axially.*—2¾" [70 mm.].
*Average diameter across suture plane.*—2 15/16" [75 mm.].
*Average diameter across cheek plane.*—2⅞" [73 mm.].
*Typical weight.*—7.9 ounces [224 grams].
Form: Uniform, globose, slightly asymmetrical.
*Longitudinal section form.*—Form to elliptical.
*Axial view.*—Round.

Suture: A shallow groove near the base, a shallow trough along the side, and a sharp groove toward the apex, ending just beyond the pistil point with a moderate depression.
Ventral surface: Rounded strongly, lipped stronger toward the apex.
Lips: Somewhat unequal.
Cavity: Flaring, circular to elongated in the suture plane, suture usually showing on both sides, Brilliant orange yellow [67. brill.OY] stem markings typical.
*Depth.*—½" [12.7 mm.].
*Breadth.*—1⅛" [28.6 mm.].
Base: Truncate.
Apex: Rounded, but somewhat cordate if viewed parallel to the suture.
Pistil point: Mostly oblique, short, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Moderately astringent.
*Tendency to crack.*—None observed.
*Color.*—Very deep red [14. v.deep R] streaking and mottling over a Very reddish orange [34. v.rO] background with a little Light yellow [86. l.Y] freckling on the sides toward the apex.
Flesh:
*Color.*—Brilliant yellow [83. brill.Y] with Deep red [13. deep R] streaking next to the stone.
*Surface of pit cavity.*—Very deep red [14. v.deep R] broken fibers when twisted from stone.
*Amygdalin.*—Abundant.
*Juice.*—Abundant, rich.
*Texture.*—Very firm, crisp.
*Fibers.*—Abundant, fine.
*Ripens.*—Slightly earlier at the apex.
*Flavor.*—Acidic and sweet, typically 14 brix.
*Aroma.*—Moderate.
*Eating quality.*—Very good.

STONE

Type: Clingstone.
Form: Oval.
Hilum: Narrow.
Base: Slightly oblique.
Apex: Acute with an average angle of 90 degrees and a ⅛" [3.2 mm.] tip.
Sides: Equal.
Surface: Irregularly furrowed toward the apex, pitted toward the base.
Ridges: Jagged.
External color: Moderate brown [58. m.Br].
Pit wall color when cracked: Moderate yellowish brown [77. m.yBr].
Cavity surface color: Deep brown [56. deep Br].
Average pit wall thickness: ¼" [6.4 mm.].
Average width: 1 3/16" [30.2 mm.].
Average length: 1 9/16" [39.7 mm.].
Average breadth: ⅞" [22.2 mm.].
Tendency to split: Slight.
Kernel:
*Form.*—Oval.
*Skin color.*—Strong yellowish brown [74. s.yBr].
*Pellicle color.*—Dark brown [59. d.Br].
*Vein color.*—Dark brown [59. d.Br].
*Taste.*—Bitter.
*Viable.*—Yes.
*Average width.*—⅝" [15.9 mm.].
*Average length.*—13/16" [20.6 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its parent, 'September Bright' (U.S. Plant Pat. No. 13,475) nectarine, by producing nectarines that are firm in texture, clingstone in type, yellow in flesh color, and mostly red in skin color, but is distinguished therefrom by producing fruit that matures about seven days later.

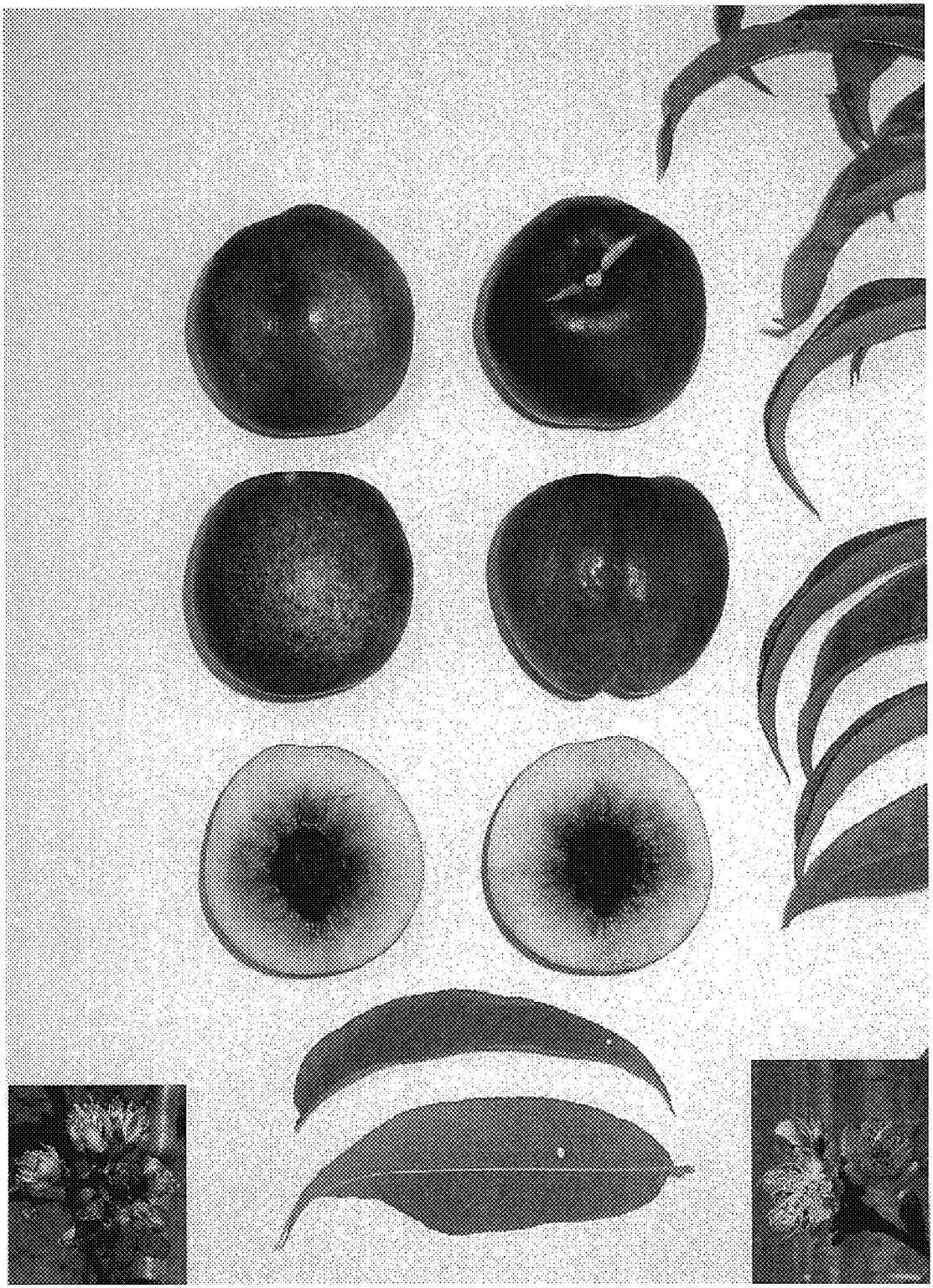

* * * * *